US009498172B2

(12) United States Patent
Lee et al.

(10) Patent No.: US 9,498,172 B2
(45) Date of Patent: Nov. 22, 2016

(54) CONTROL DEVICES RECEIVING USERS' COMMANDS AND MEDICAL APPARATUSES INCLUDING THE SAME

(71) Applicant: SAMSUNG ELECTRONICS CO., LTD., Suwon-si, Gyeonggi-do (KR)

(72) Inventors: Young-jun Lee, Seoul (KR); Dae-soo Kim, Yongin-si (KR); Hyung-won Yoon, Seoul (KR); Ji-na Jeon, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 325 days.

(21) Appl. No.: 14/163,479

(22) Filed: Jan. 24, 2014

(65) Prior Publication Data

US 2014/0328469 A1 Nov. 6, 2014

(30) Foreign Application Priority Data

May 2, 2013 (KR) .................. 10-2013-0049620

(51) Int. Cl.
*A61B 6/00* (2006.01)
(52) U.S. Cl.
CPC ................. *A61B 6/44* (2013.01); *A61B 6/467* (2013.01); *A61B 6/502* (2013.01)
(58) Field of Classification Search
CPC ............... A61B 2017/00973; A61B 17/1626; A61B 2017/00367; A61B 19/56
USPC .................................. 378/204, 205
See application file for complete search history.

(56) References Cited

U.S. PATENT DOCUMENTS

| | | | | |
|---|---|---|---|---|
| 6,051,797 A * | 4/2000 | Meinel | ................... | H01H 21/26 200/86.5 |
| 7,331,711 B2 | 2/2008 | Sandkamp et al. | | |
| 7,756,245 B2 * | 7/2010 | Kanemitsu | ............... | A61B 6/04 378/208 |
| 7,809,111 B2 * | 10/2010 | Meer | ...................... | A61B 6/467 378/114 |
| 8,143,540 B2 * | 3/2012 | Twellman | ................ | H01H 3/14 200/86.5 |
| 8,861,813 B2 * | 10/2014 | Levasseur, Jr. | ....... | A61B 6/0457 382/100 |
| 2009/0190715 A1 * | 7/2009 | Meer | ...................... | A61B 6/502 378/37 |
| 2009/0216189 A1 | 8/2009 | Gasser et al. | | |
| 2010/0230259 A1 * | 9/2010 | Jo | .......................... | G05G 1/445 200/86.5 |

FOREIGN PATENT DOCUMENTS

| | | |
|---|---|---|
| JP | 2011-152327 | 8/2011 |
| JP | 2012-80979 | 4/2012 |
| KR | 10-0971418 | 7/2010 |

OTHER PUBLICATIONS

Korean Office Action dated Aug. 25, 2014 From Korean Patent Application No. 10-2013-0049620, 11 pages.

* cited by examiner

*Primary Examiner* — Michael Maskell
(74) *Attorney, Agent, or Firm* — Staas & Halsey LLP

(57) ABSTRACT

A user control device may include a manipulation panel which receives an external force or input from a manipulating input or device, a frame that is spaced apart from the manipulation panel and having an accommodating unit accommodating the manipulation panel, and a sensing unit disposed in the accommodating unit to sense a movement of the manipulation panel. The manipulation panel may be three-dimensionally movable according to a movement of the manipulating input or device. Related medical apparatuses may also be controlled using the user control device.

25 Claims, 8 Drawing Sheets

CONTROL DEVICES RECEIVING USERS' COMMANDS AND MEDICAL APPARATUSES INCLUDING THE SAME

CROSS-REFERENCE TO RELATED APPLICATIONS

This application claims the priority benefit of Korean Patent Application No. 10-2013-0049620, filed on May 2, 2013, in the Korean Intellectual Property Office, the disclosure of which is incorporated herein in its entirety by reference.

BACKGROUND

1. Field

The disclosure herein relates to medical apparatuses, and more particularly, to control devices receiving users' commands and medical apparatuses including the same.

2. Description of the Related Art

Magnetic resonance imaging (MRI) apparatuses, computed tomography (CT) apparatuses, and X-ray apparatuses have been widely used as medical apparatuses that obtain medical images of objects or bodies, including a human body or animal body. These apparatuses may take a picture (capture an image) of a portion of the body or the whole body according to an image resolution or an apparatus size. Further, the apparatuses may take a picture of the whole portion of the object or human or animal body at a time. Alternatively, the apparatuses may take pictures of portions of the object or body separately and may synthesize the separate pictures to produce a single image of the whole object or body.

Some components used in taking a picture of the object or body have to be appropriately moved in order for the medical apparatuses to obtain medical images. Accordingly, control devices receiving users' commands have been continuously developed to spatially move the components of the medical apparatuses.

SUMMARY

Additional aspects and/or advantages will be set forth in part in the description which follows and, in part, will be apparent from the description, or may be learned by practice of the invention.

The present invention provides control devices receiving users' commands and medical apparatuses including the same.

According to an aspect of the disclosure, there is provided a user control device including a manipulation panel on which a manipulating means (e.g., an external force, external input, external manipulator, and the like) is placed, a frame that is spaced apart from the manipulation panel and having an accommodating unit accommodating the manipulation panel, and a sensing unit disposed in the accommodating unit to sense a movement of the manipulation panel. The manipulation panel is three-dimensionally movable according to a movement of the manipulating means (e.g., an external force, external input, external manipulator, and the like).

The frame may include a bottom portion and a sidewall upwardly protruding from an edge of the bottom portion, and the accommodating unit may be defined by the sidewall and the bottom portion of the frame.

The manipulation panel may be movable in a horizontal direction parallel with the bottom portion of the frame or in a vertical direction parallel with the sidewall of the frame.

The manipulation panel may have a flat board shape.

The sensing unit may be disposed on at least one of the frame and the manipulation panel.

The user control device may further include an auxiliary unit that is disposed in the accommodating unit to assist movement of the manipulation panel.

The manipulation panel may be connected to the auxiliary unit if the manipulating means (e.g., an external force, external input, external manipulator, and the like) is placed on or applied to the manipulation panel, and the manipulation panel may be disconnected from the auxiliary unit if the manipulating means (e.g., an external force, external input, external manipulator, and the like) is lifted or removed from the manipulation panel.

The auxiliary unit may include an elastic portion that returns the manipulation panel to its original position when the manipulating means (e.g., an external force, external input, external manipulator, and the like) is lifted or removed from the manipulation panel.

The device may receives users' commands for spatially moving at least one element of a medical apparatus.

For example, the manipulating means (e.g., an external force, external input, external manipulator, and the like) may be a user's foot, a stick, or any input or mechanism that may exert pressure or force to the manipulation panel.

According to another aspect of the disclosure, there is provided a medical apparatus including a user control device and a driver. The user control device includes a manipulation panel on which a manipulating means (e.g., an external force, external input, external manipulator, and the like) is placed or applied and a frame being spaced apart from the manipulation panel and having an accommodating unit accommodating the manipulation panel therein. The driver spatially moves photograph members in response to movement of the manipulation panel.

The manipulation panel may three-dimensionally move in the accommodating unit.

The photograph members may linearly move if the manipulation panel linearly moves.

The photograph members may rotate if the manipulation panel rotates.

For example, if the manipulation panel moves in a first direction, the photograph members may move in a second direction. In addition, if the manipulation panel moves in a third direction different from the first direction, the photograph members may move in a fourth direction different from the second direction.

For example, if the manipulation panel moves in a direction between the first direction and the third direction, the photograph members may rotate.

For example, the manipulation panel may move in the first or second direction after moving in a fifth direction.

The fifth direction may be a direction that the manipulation panel moves toward a bottom portion of the frame The medical apparatus may further include an auxiliary unit that is disposed in the accommodating unit to assist movement of the manipulation panel.

The auxiliary unit may include an elastic portion that returns the manipulation panel to its original position if the manipulating means (e.g., an external force, external input, external manipulator, and the like) is lifted from the manipulation panel.

According to another aspect of the disclosure, there is provided a user control device including a frame having a bottom portion and at least one side wall extending upward from the bottom portion, an auxiliary unit connected to the frame and disposed within an inner portion of the frame, a manipulation panel, supported by the auxiliary unit, to move three-dimensionally according to an external force applied to the manipulation panel, and at least one sensor disposed within the frame to sense movement of the manipulation panel.

The auxiliary unit may include an elastic unit to return the manipulation panel to an original position after an external force applied to the manipulation panel is removed. The elastic unit may be connected to at least one side wall of the frame, and at least one sensor may be disposed on the bottom portion of the frame.

The auxiliary unit may further include a supporting unit to support the manipulation panel, and the supporting unit and manipulation panel may be spaced apart from one another when an external force applied to the manipulation panel is removed, and the manipulation panel may move toward the supporting unit to contact the supporting unit when an external force is applied to the manipulation panel. The supporting unit may be ball-shaped, and the manipulation panel may include a hole corresponding to a position of the supporting unit The auxiliary unit may further include a connecting unit to surround at least a portion of the supporting unit, and the elastic unit may be fixed to the connecting unit.

The user control device may be connected to a medical apparatus, and one or more elements of the medical apparatus may be moved in response to movement of the manipulation panel sensed by the at least one sensor. The one or more elements may include at least one of a gantry, x-ray generator, x-ray detector, and a photograph panel.

According to another aspect of the disclosure, there is provided a method of controlling movement of at least one photograph member disposed at a medical apparatus, the method including: applying a force to a manipulation panel of a user control device connected to the medical apparatus, sensing, by at least one sensor disposed within a frame of the user control device, a movement direction of the manipulation panel, and controlling the at least one photograph member to move in a predefined direction in response to the sensed movement direction of the manipulation panel.

The method may further include transmitting, by the user control device, a command to a driver of the medical apparatus to move the at least one photograph member, and moving, by the driver, the at least one photograph member for a time or distance proportional to a sensing time of the at least one sensor.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION

Figure 1:
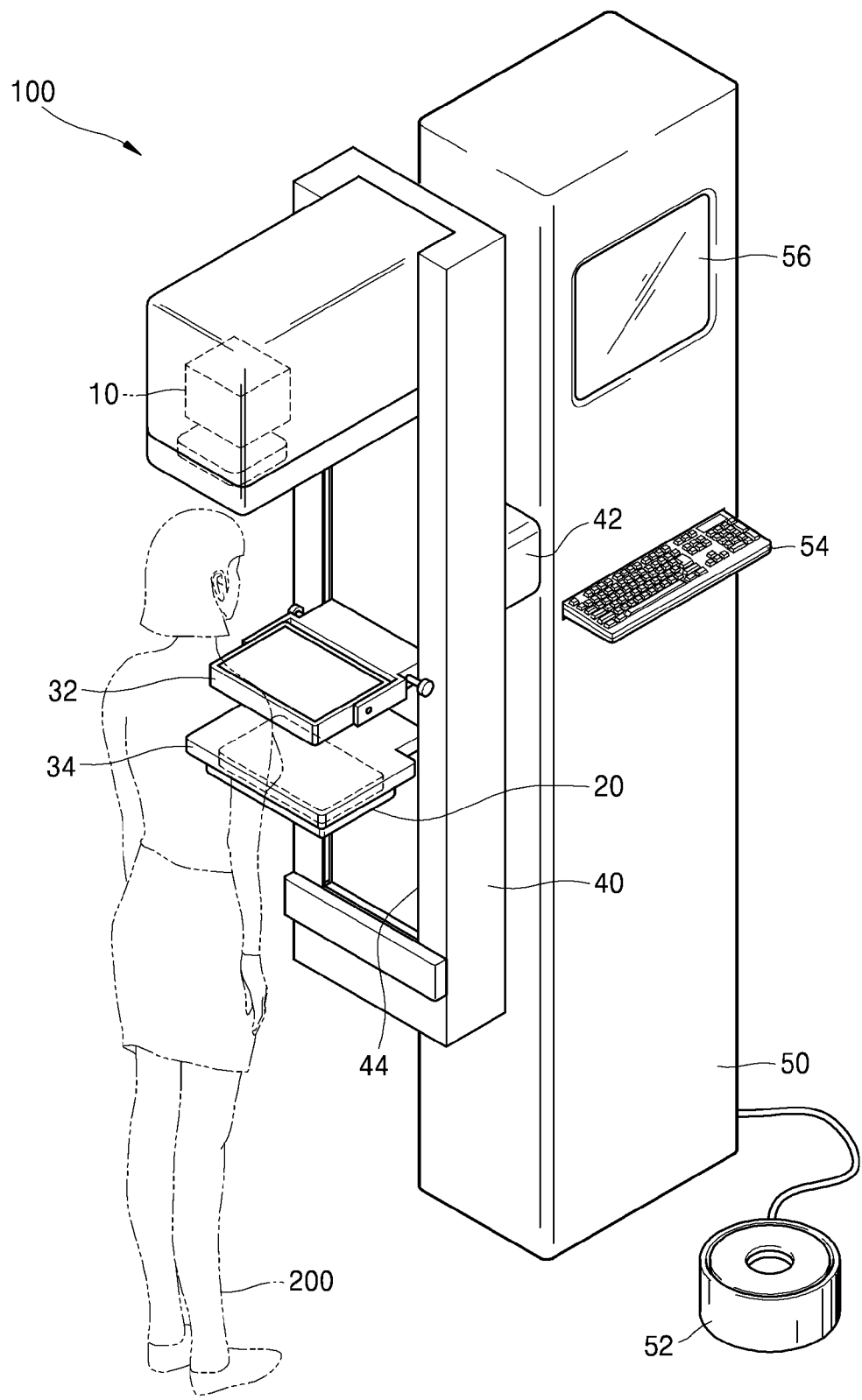
FIG. 1 is a perspective view illustrating an external appearance of a medical apparatus according to an embodiment of the present invention.

Example embodiments of user control devices and medical apparatuses including the same will now be described more fully hereinafter with reference to the accompanying drawings, in which example embodiments are shown. Like reference numerals in the drawings denote like elements, and thus their description will be omitted. Expressions such as "at least one of," when preceding a list of elements, modify the entire list of elements and do not modify the individual elements of the list.

In the present specification, the term "object" may include a physical object (e.g., a suitcase, container, and the like, or portions thereof), a human body, an animal body, a portion of the human body, or a portion of the animal body, and the like. For example, the term "object" may include a liver, a heart, a uterus, a brain, a mamma, a blood vessel or the like. Further, the term "user" used herein may include medical experts, for example, medical doctors, nurses, medical laboratory technologists, medical imaging specialists, technicians for fixing medical apparatuses, or the like, but the term is not limited thereto. Generally, a user may refer to any user or operator, and need not be a medical professional.

FIG. 1 is a perspective view illustrating an external appearance of a medical apparatus 100 according to an embodiment of the present invention. For example, the medical apparatus 100 shown in FIG. 1 may be a mammography apparatus for taking a picture (capturing a image) of a mamma. However, the medical apparatus according to embodiments of the present invention is not limited to the mammography apparatus. That is, the embodiments of the present invention may be applied to all apparatuses for taking a picture of an object. For example, the embodiments disclosed herein may be applied to any apparatus which captures an image of an object, such as an image depicting internal features of the object.

As illustrated in FIG. 1, the medical apparatus 100 may include an X-ray generator 10 and an X-ray detector 20 for receiving X-rays that penetrate an object 200 between the X-ray generator 10 and the X-ray detector 20. The medical apparatus 100 may further include first and second photograph panels 32 and 34 on which the object 200 can be safely placed in order to take a picture of the object 200 using the X-ray generator 10 and the X-ray detector 20. The X-ray generator 10, the X-ray detector 20, and the first and second photograph panels 32 and 34 may be elements used to take a picture of the object 200 with X-rays. Thus, the X-ray generator 10, the X-ray detector 20, and the first and second photograph panels 32 and 34 may be referred to as photograph members. Moreover, the medical apparatus 100 may further include a gantry 40 supporting the X-ray generator 10, the X-ray detector 20, and the first and second photograph panels 32 and 34, and a main body 50 supporting the gantry 40.

The main body 50 may include a plurality of controllers (e.g., first and second user controllers 52 and 54) for receiving a user's commands for operation of the medical apparatus 100, a display unit 56 displaying X-ray-based images, and a controller (not shown) controlling overall operations of the medical apparatus 100. In example embodiments, the first and second user controllers 52 and 54, the display unit 56 and the controller may not be included in the main body 50. For example, the user control devices 52 and 54, the display unit 56, and the controller may be implemented by using external devices that communicate with the medical apparatus 100 by a wireless or wired (e.g., cable) connection, or a combination thereof.

The first and second controllers 52 and 54 may receive instructions input by a user or operator, such as, for example, an instruction for selection of an operation of the medical apparatus, including operations related to the X-ray generator 10, X-ray detector 20, first and second photograph panels 32 and 34, gantry 40, and/or display unit 56. One or more controllers may be embodied as a haptic device, clutch pedal, switch, button, voice recognition device, keys, joystick, keyboard, mouse, touch screen, or combinations thereof, which may be used to enable a user to control the medical apparatus and elements thereof.

The display unit 56 may be embodied by, for example, a Liquid Crystal Display (LCD), light emitting diode (LED) display, organic light emitting diode (OLED) display, plasma display panel (PDP), cathode ray tube (CRT), and the like. While FIG. 1 shows a single display unit 56, the disclosure is not so limited. There may be two or more display units 56 included in the main body 50 of the medical apparatus 100.

The first and second user controllers 52 and 54 may respectively include a user controller controlling spatial movements of the medical apparatus 100 and a user controller controlling signal processing operations necessary for taking a picture. If a motion of the user handling the first user controller 52 has a relation with the spatial movements of the medical apparatus 100, the user may readily control the medical apparatus 100. A detailed structure of the first user controller 52 will be described later.

The gantry 40 may be attached to the main body 50 through a gantry driver 42. The gantry 40 may be disposed on a sidewall of the main body 50 along a vertical direction. The gantry driver 42 may operate according to a user's commands, which may be inputted through the first user controller 52. For example, the gantry driver 42 may rotate the gantry 40 by a certain angle or 360 degrees. In addition, the gantry driver 42 may move the gantry 40 up or down. As such, the gantry 40 may be upwardly or downwardly moved by the gantry driver 42 along a vertical direction of the main body 50 to thus control a height of the gantry 40. Further, the gantry 40 may be rotated by the gantry driver 42.

The first and second photograph panels 32 and 34, which may be in contact with the object 200, may be disposed on a front surface of the gantry 40 opposite to the main body 50. With reference to FIG. 1, the gantry 40 may have a front surface and a rear surface, on an opposite side of the front surface. The front surface may accommodate or hold the x-ray generator 10, for example at an upper portion thereof. The first and second photograph panels 32 and 34 may be moved up or down along a guide groove 44 in the front surface of the gantry 40. For example, the first and second photograph panels 32 and 34 may be parallel with one another with respect to each other in a vertical direction. The rear surface of the gantry 40 may be connected to the gantry driver 42, and may face a side surface or other surface of the main body 50. Accordingly, if the object 200, for example, a mamma of the object 200, is positioned between the first and second photograph panels 32 and 34, at least one of the first and second photograph panels 32 and 34 may press and compress the mamma of the object 200. For instance, the second photograph panel 34 may be moved up or down to place the mamma of the object 200 thereon, and the first photograph panel 32 may be moved down to press and compress the mamma of the object 200.

The X-ray generator 10 for generating X-rays may be provided over (above) the first photograph panel 32 opposite to the second photograph panel 34. As such, the X-ray generator 10 may generate X-rays toward the mamma of the object 200 while the mamma of the object 200 is pressed by the first photograph panel 32. The X-ray generator 10 may include a single X-ray source to radiate X-rays emitted from the single X-ray source in all directions. Alternatively, the X-ray generator 10 may include a plurality of X-ray sources to radiate X-rays emitted from the plurality of X-ray sources in one direction. The X-ray generator 10 may be fixed to the gantry 40 so as not to be moved. Alternatively, the X-ray generator 10 may be moved along the guide groove 44.

The X-ray detector 20 may be positioned under the second photograph panel 34 opposite to the first photograph panel 32 to receive and detect the X-rays penetrating the object 200, for example, the mamma of the object 200. The X-ray detector 20 may be disposed to be spaced apart from the second photograph panel 34 by a certain distance. In such a case, the X-ray detector 20 may get closer to or further from the object 200 if the second photograph panel 34 moves. For example, the X-ray detector 20 and the second photograph panel 34 may be integrated to move together with each other when the gantry 40 moves along the guide groove 44. The X-ray detector 20 may be disposed to contact a bottom surface of the second photograph panel 34 in order to minimize a distance between the X-ray detector 20 and the object 200. Further, the X-ray detector 20 may include a plurality of X-ray detecting units (not shown) that are two-dimensionally arrayed on a flat plane.

As described above, the photograph members (e.g., the X-ray generator 10, the X-ray detector 20, and the first and second photograph panels 32 and 34) of the medical apparatus 100 may be spatially moved according to user's commands which are inputted through the first user controller 52. The X-ray generator 10, the X-ray detector 20, and the first and second photograph panels 32 and 34 constituting the photograph members may be simultaneously or independently moved. Because the photograph members move in a three-dimensional space, the user may readily control the movements of the photograph members if a movement of the first user controller 52 or a motion of the user handling the first user controller 52 is similar to the movements of the photograph members.

Hereinafter, a structure of the first user controller 52, which is closely related with motions of the user or movements of the photograph members, will be described. For the purpose of ease and convenience in explanation, the first user controller 52 may be referred to as a user control device.

Figure 2A:
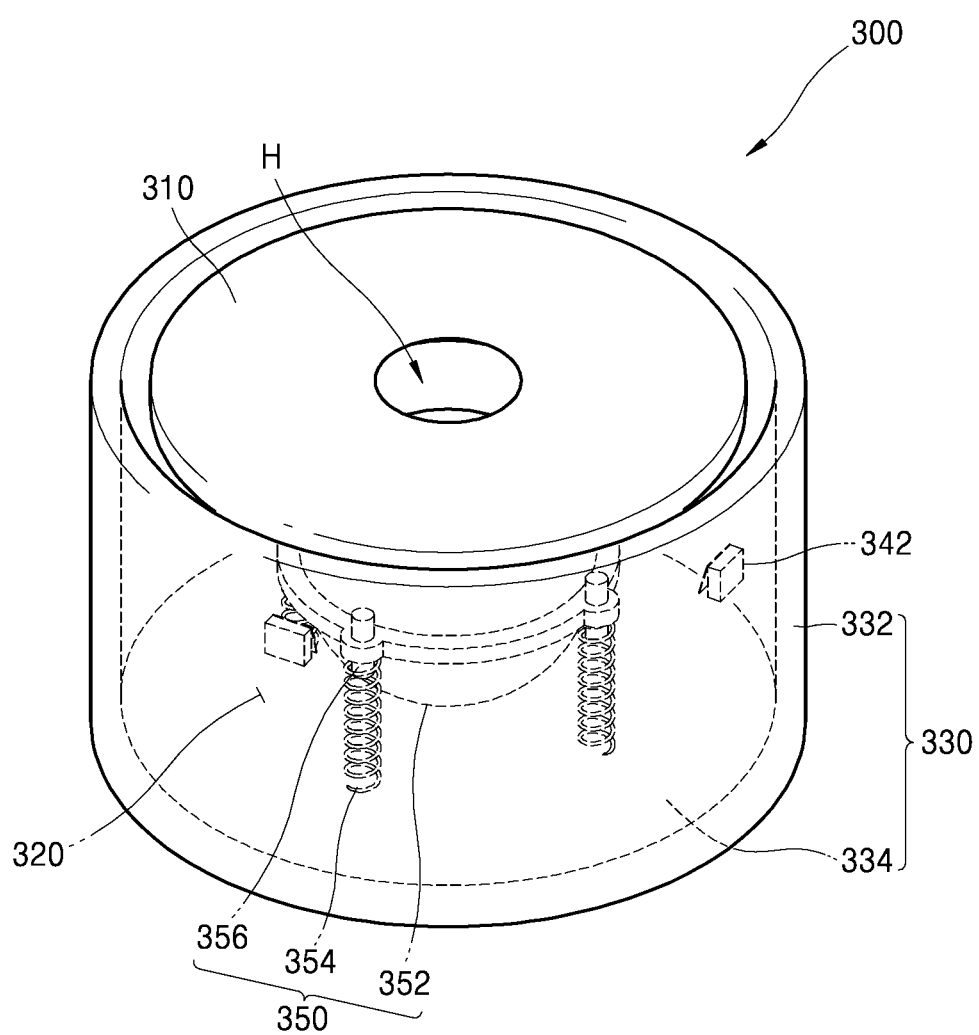
FIG. 2A is a schematic view illustrating a user control device according to an embodiment of the present invention.
Figure 2B:
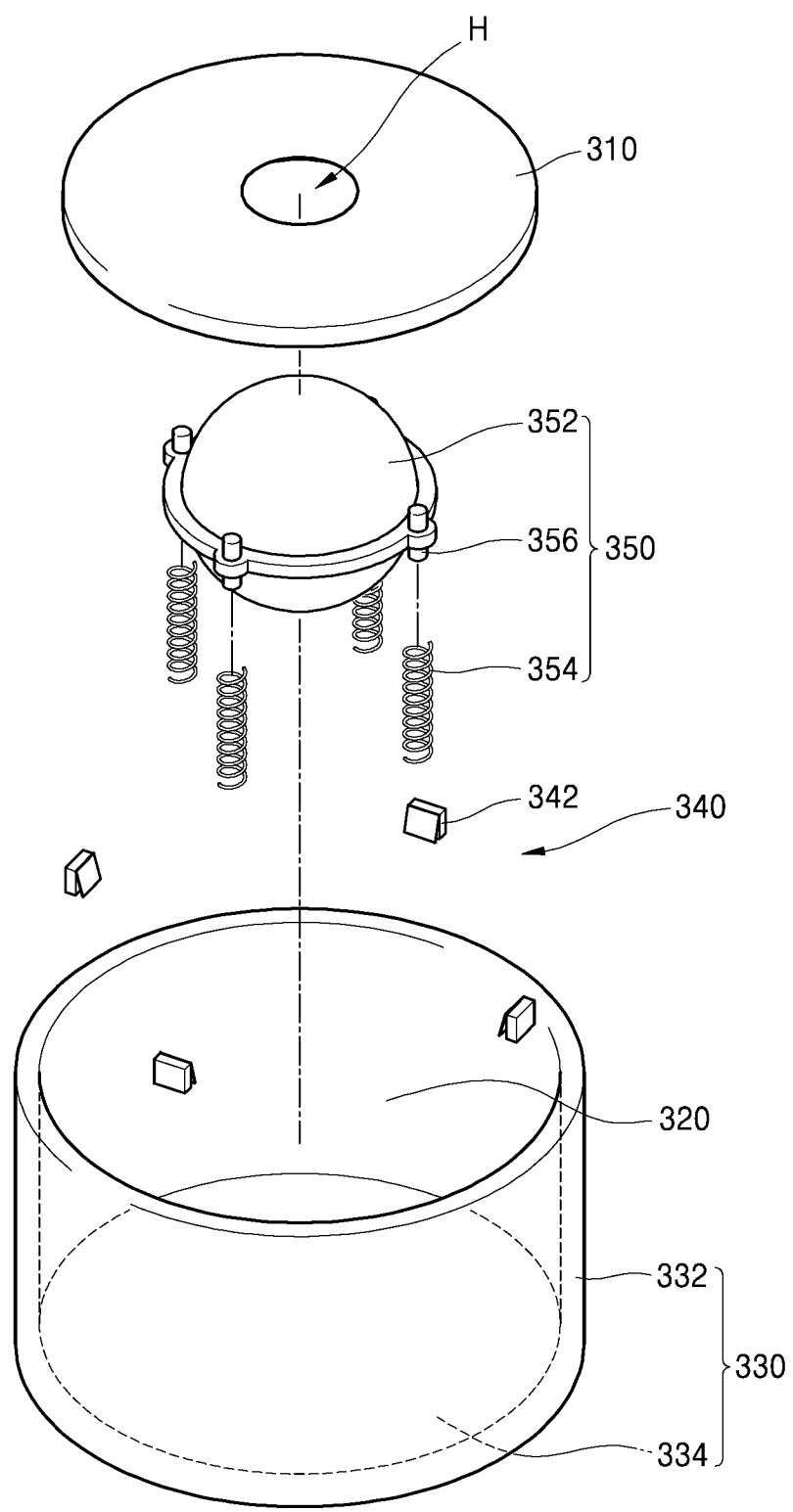
FIG. 2B is an exploded perspective view illustrating the user control device of FIG. 2A.

FIG. 2A is a schematic view illustrating a user control device 300 according to an embodiment of the present invention, and FIG. 2B is an exploded perspective view illustrating the user control device 300 of FIG. 2A.

As illustrated in FIGS. 2A and 2B, the user control device 300 may include a manipulation panel 310 on which a manipulating means (manipulating input or manipulator) 400 (see e.g., FIGS. 4 through 7) may be placed and a frame 330 in which the manipulation panel 310 is located. The manipulating input may refer to any input or object which is applied or directed toward the manipulation panel 310 to control a device associated with the medical apparatus. The manipulating input may be, for example, a user's foot, hand, and the like, and/or any input device such as a stick, for example. The frame 330 may be spaced apart from the manipulation panel 310 and may have an accommodating unit 320 that can accommodate the manipulation panel 310. Further, the user control device 300 may include a sensing unit 340 disposed in the accommodating unit 320. The sensing unit 340 may sense a movement of the manipulation panel 310. The sensing unit 340 may include a plurality of sensors 342 that are two-dimensionally arrayed. As such, the manipulation panel 310 may be moved according to a motion of the manipulating means 400 placed on or directed toward the manipulation panel 310, and at least one of the plurality of sensors 342 may sense a movement of the manipulation panel 310.

The manipulation panel 310 may have a flat board shape, and the manipulating means (manipulating input) 400 may be placed on or directed toward the manipulation panel 310. The manipulating means (manipulating input) 400 may be a foot of the user. However, the present invention is not limited thereto, and, for example, the manipulating means (manipulating input) 400 may be a user's hand, a stick, or the like.

The frame 330 may include a bottom portion 334 and a sidewall 332 upwardly protruding from an edge of the bottom portion 334. The accommodating unit 320 may correspond to a space that is surrounded by the sidewall 332 and the bottom portion 334. The manipulation panel 310 may be disposed in the accommodating unit 320. Since the frame 330 is spaced apart from the manipulation panel 310, the manipulation panel 310 may be three-dimensionally movable within the accommodating unit 320. For example, the manipulation panel 310 may be moved in every direction. For example, the manipulation panel 310 may be moved back and forth, to the left and right, and/or up and down, within the accommodating unit 320. Of course, the disclosure is not limited to the above-described directions, and the manipulation panel 310 may be moveable in any direction. In a plan view, the manipulation panel 310 and the frame 330 may have a circular shape such that the manipulation panel 310 is freely movable in the frame 330. However, the present invention is not limited thereto, and, for example, the manipulation panel 310 and the frame 330 may be formed in any shape. For example, the manipulation panel 310 and the frame 330 may have a polygonal shape, a rectangular shape, or an oval shape or other geometric shape, in a plan view. In some embodiments, the planar shapes of the manipulation panel 310 and the frame 330 may be modified according to the movement of the manipulation panel 310.

The user control device 300 may further include an auxiliary unit 350 assisting a movement of the manipulation panel 310. The auxiliary unit 350 may be disposed in the accommodating unit 320. For example, the auxiliary unit 350 may be disposed between the manipulation panel 310 and the bottom portion 334 of the frame 330. As such, the manipulation panel 310 may be connected to the auxiliary unit 350 if the manipulating means (manipulating input) 400 is placed on the manipulation panel 310, and the manipulation panel 310 may be disconnected from the auxiliary unit 350 if the manipulating means (manipulating input) 400 is lifted or removed from the manipulation panel 310.

The auxiliary unit 350 may include a supporting unit 352 for supporting the manipulation panel 310, elastic unit 354 for restoring a position of the manipulation panel 310, and one or more (e.g., four) connecting units 356 for connecting the supporting unit 352 to the elastic units 354. The supporting unit 352 may be disposed between the manipulation panel 310 and the bottom portion 334 of the frame 330. The supporting unit 352 may be in contact with the bottom portion 334 of the frame 330 or may be spaced apart from the bottom portion 334 of the frame 330 by a predetermined distance. The manipulation panel 310 may be moved down toward the bottom portion 334 of the frame 330 until the manipulation panel 310 contacts the supporting unit 352.

The supporting unit 352 may have a ball-shaped configuration (e.g., spherically shaped). Balls may be readily movable in every (any) direction. Thus, the supporting unit 352 having a ball-shaped configuration may assist the manipulation panel 310 to smoothly move. The manipulation panel 310 may have a hole H which is located at a position (e.g., a central position) corresponding to the supporting unit 352. As such, the manipulation panel 310 may be easily connected to the supporting unit 352 because of the presence of the hole H. The hole H may be formed in the manipulation panel 310 at a center position or location of the supporting unit 352 and/or manipulation panel 310. The shape of the supporting unit 352 is not limited to a ball-shaped configuration. For example, the supporting unit 352 may have a different shape from a ball. In some embodiments, the supporting unit 352 may have a pillar-shaped configuration.

The elastic units 354 may prevent an abrupt movement of the manipulation panel 310 and may restore a position of the manipulation panel 310 to an original position thereof if the manipulation of the manipulation panel 310 terminates. Each of the elastic units 354 may be a spring. However, the present invention is not limited thereto, and each of the elastic units 354 may be implemented by using any member having an elastic property. Referring to FIG. 2A, little or no force or pressure may be applied to the manipulation panel and elastic units 354 may not be compressed, such that the manipulation panel 310 is disposed above the supporting unit 352. Referring to FIG. 2B, a larger force or pressure may be applied to the manipulation panel and elastic units 354 may be compressed, such that manipulation panel 310 is disposed to move toward and/or contact at least a portion of the supporting unit 352.

The connecting units 356 may be disposed to surround some portions of the supporting unit 352, and the elastic units 354 may be respectively fixed to the connecting units 356. According to FIGS. 2A and 2B, the auxiliary unit 350 may be configured to, adapted to, suitable for, capable of, operable to, etc., include the supporting unit 352, the elastic units 354 and the connecting units 356. However, at least three kinds of elements, that is, the supporting unit 352, the elastic units 354 and the connecting units 356, may not be indispensable to the auxiliary unit 350. For example, the auxiliary unit 350 may include at least one kind of element among the supporting unit 352, the elastic units 354 and the connecting units 356 according to a design scheme of the auxiliary unit 350.

As described above, the user control device 300 may include the sensing unit 340, which is disposed in the accommodating unit 320 and senses a movement of the manipulation panel 310. Further, the sensing unit 340 may include a plurality of sensors 342, as illustrated in FIGS. 2A and 2B. According to FIGS. 2A and 2B, the plurality of sensors 342 may be disposed adjacent to the sidewall 332 of the frame 330. However, the present invention is not limited thereto and, according to some embodiments, the plurality of sensors 342 may be disposed on the connecting units 356 or the manipulation panel 310. Moreover, according to FIGS. 2A and 2B, the user control device 300 may be configured to, adapted to, suitable for, capable of, operable to, etc., include four sensors 342. However, the present invention is not limited thereto, and the number of sensors 342 may be determined according to the degree of accuracy at which the movement of the manipulation panel 310 is to be sensed. In embodiments, the plurality of sensors 342 may be two or three-dimensionally arrayed to sense a two- or three-dimensional movement of the manipulation panel 310.

One or more (e.g., a plurality or all) of the sensors 342 may be embodied as a micro switch. However, the present invention is not limited thereto, and one or more or each of the sensors 342 may generally be referred to as any sensor that may sense the movement of the manipulation panel 310. For example, each of the sensors 342 may be a photo sensor or a piezoelectric sensor.

Figure 3A:
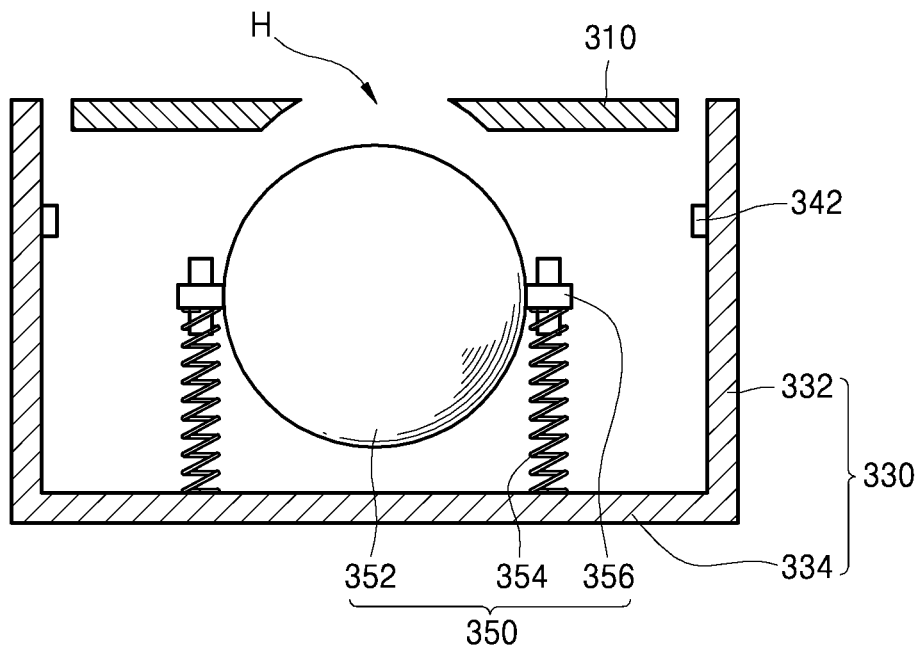
FIG. 3A is a cross-sectional view illustrating an initial mode state of the user control device shown in FIG. 2A.
Figure 3B:
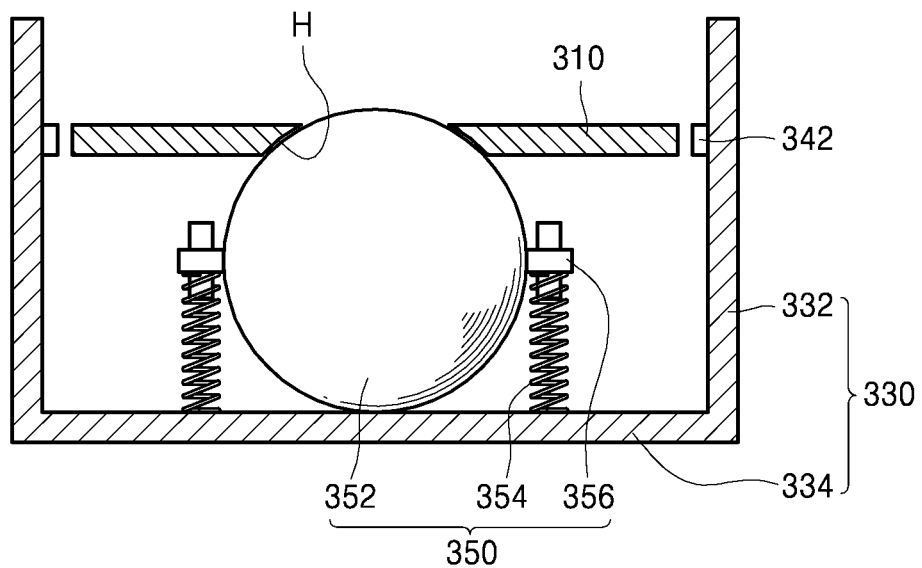
FIG. 3B is a cross-sectional view illustrating a standby mode state of the user control device shown in FIG. 2A.

FIG. 3A is a cross-sectional view illustrating an initial mode state of the user control device 300 shown in FIG. 2A, and FIG. 3B is a cross-sectional view illustrating a standby mode state of the user control device 300 shown in FIG. 2A.

The term "initial mode" used herein may correspond to a state that the manipulating means (manipulating input) 400 is not placed on or applied to the manipulation panel 310 of the user control device 300. As illustrated in FIG. 3A, when the user control device 300 is under the initial mode, the manipulation panel 310 may be disconnected from (spaced apart from) the auxiliary unit 350. In the initial mode of the user control device 300, no pressure is applied to the manipulation panel 310. Thus, the elastic units 354 may maintain their original position due to an elastic coefficient thereof. As a result, the supporting unit 352 may be spaced apart from the bottom portion 334 of the frame 330.

If the manipulating means (manipulating input) 400, for example, a foot of the user, is placed on or applied to the manipulation panel 310, the manipulation panel 310 may move down towards the bottom portion 334 of the frame 330 as illustrated in FIG. 3B. When the supporting unit 352 is combined with the hole H formed in the manipulation panel 310, the downward movement of the manipulation panel 310 may be stopped. If the downward movement of the manipulation panel 310 is stopped, the user may recognize the user control device 300 to be under a standby mode. In some embodiments, the user control device 300 may further include at least one additional sensor 342 on the bottom portion 334 of the frame 330. As such, if the supporting unit 352 contacts the additional sensor 342 on the bottom portion 334, the controller of the medical apparatus 100 may also recognize the user control device 300 to be under the standby mode. The controller of the medical apparatus 100 may inform the user that the user control device 300 is in the standby mode, visually (e.g., by light) or sound. Additionally, or alternatively, the controller of the medical apparatus 100 may also recognize the user control device 300 to be under the standby mode when a sensor, disposed adjacent to a sidewall of the frame 330, detects the presence of the manipulation panel 310.

If the manipulating means (manipulating input) 400 is lifted or removed from the manipulation panel 310, the manipulation panel 310 may be disconnected (spaced apart) from the auxiliary unit 350. That is, due to the lifting or removal of the manipulating means (manipulating input) 400 from the manipulation panel 310, the elastic units 354 may return to their original position due to their elastic property. As a result, the manipulation panel 310 may move up to be further from the bottom portion 334 of the frame 330, and the manipulation panel 310 may be disconnected or spaced apart from the supporting unit 352 as illustrated in FIG. 3A.

As illustrated in FIG. 1, the X-ray generator 10, the X-ray detector 20, and the first and second photograph panels 32 and 34 may be attached to the gantry 40. Thus, if the gantry 40 moves, the X-ray generator 10, the X-ray detector 20, and the first and second photograph panels 32 and 34 may also be simultaneously moved. Hereinafter, a method of moving the gantry 40 by using the user control device 300 will be described. However, the following description is merely for convenience of explanation, and, in some embodiments, the X-ray generator 10, the X-ray detector 20, and the first and second photograph panels 32 and 34 may be independently moved using the user control device 300.

Figure 4:
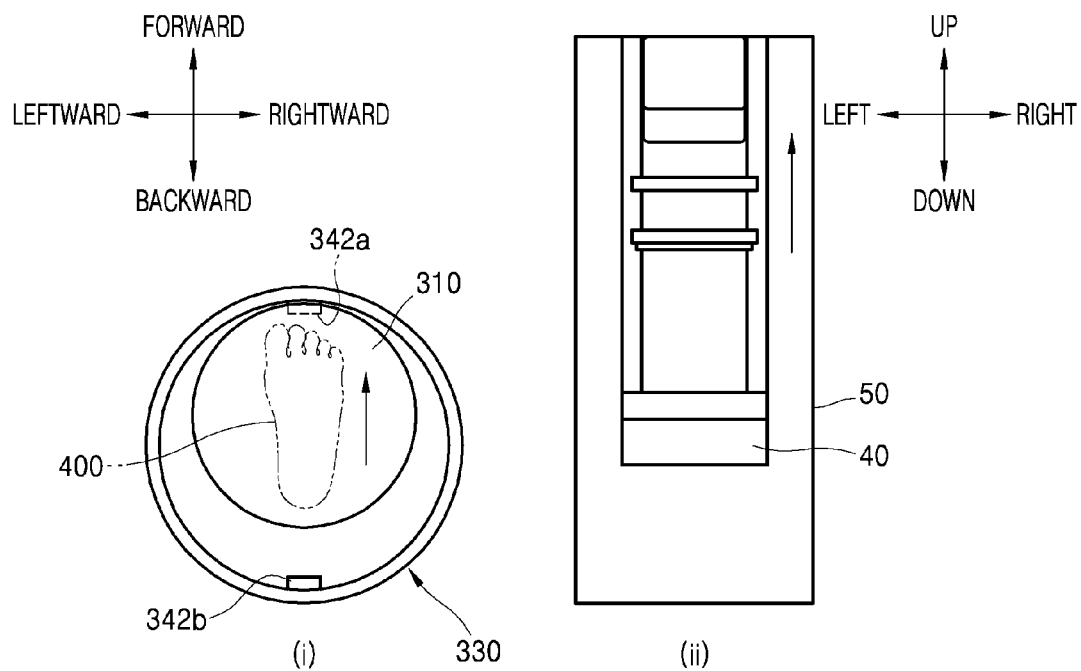
FIGS. 4 and 5 are schematic views illustrating a method of linearly moving a gantry of the medical apparatus shown in FIG. 1 using the user control device according to an embodiment of the present invention.
Figure 5:
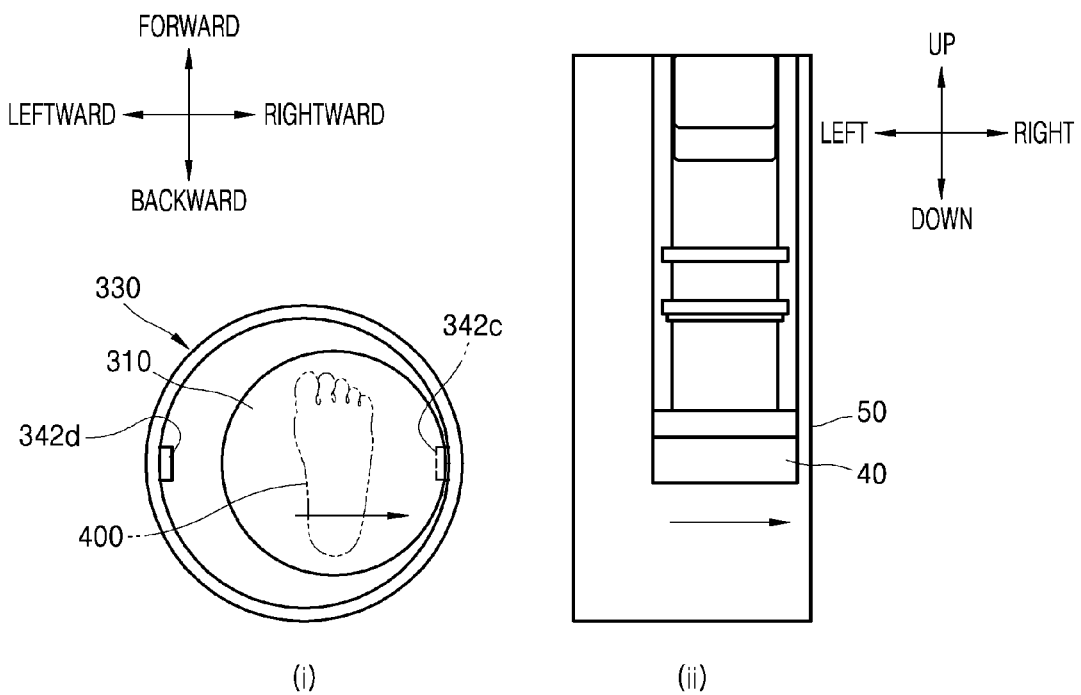

FIGS. 4 and 5 are schematic views illustrating a method of linearly moving the gantry 40 by using the user control device 300, according to an embodiment of the present invention.

When the user control device 300 is under a standby mode, the manipulation panel 310 may be moved in a forward direction if the user moves a manipulating means (manipulating input) 400, such as a user's foot, in a forward direction as illustrated in (i) of FIG. 4. As a result, a sensor 342a disposed at a front inner side of the frame 330 may contact the manipulation panel 310. In such a case, the sensor unit, including the sensor 342a, may inform the controller of the result, and the controller may recognize that a user's command for moving the gantry 40 in an upward direction has been inputted and may transmit the user's command to the gantry driver 42. The gantry driver 42 may then move the gantry 40 in an upward direction, as illustrated in (ii) of FIG. 4. A moving distance or a moving time of the gantry 40 may be proportional to a sensing time of the sensor 342a. For example, the gantry 40 may move up at a certain speed until the sensing time of the sensor 342a terminates. Additionally, or alternatively, the gantry or photograph member may be moved at a speed which reflects or is in proportion to, a degree or amount of pressure applied to the manipulation panel 310. The gantry or photograph member may be moved at a constant speed or a variable speed. Further, the gantry or photograph member may stop moving after a predetermined amount of time, after a predetermined amount of movement, and/or after the gantry has reached a limit position. In another embodiment, the direction in which the gantry or photograph member moves may be opposite to the direction in which the manipulation panel 310 is moved. For example, forward movement of the manipulation panel 310 may result in a downward movement of the gantry or photograph member.

In the standby mode of the user control device 300, the manipulation panel 310 may be moved in a backward direction if the user moves the manipulating means (manipulation unit) 400 in a backward direction. As a result, a sensor 342b disposed at a back inner side of the frame 330 may contact the manipulation panel 310. In such a case, the sensor unit, including the sensor 342b, may inform the controller of the result, and the controller may recognize that a user's command for moving the gantry 40 in a downward direction has been inputted and may transmit the user's command to the gantry driver 42. The gantry driver 42 may then move the gantry 40 in a downward direction. Additionally, or alternatively, the gantry or photograph member may be moved at a speed which reflects or is in proportion to, a degree or amount of pressure applied to the manipulation panel 310. The gantry or photograph member may be moved at a constant speed or a variable speed. Further, the gantry or photograph member may stop moving after a predetermined amount of time, after a predetermined amount of movement, and/or after the gantry has reached a limit position. In another embodiment, the direction in which the gantry or photograph member moves may be opposite to the direction in which the manipulation panel 310 is moved. For example, backward movement of the manipulation panel 310 may result in an upward movement of the gantry or photograph member.

In the standby mode of the user control device 300, the manipulation panel 310 may be moved in a rightward direction if the user moves the manipulating means 400, such as a user's foot, in a rightward direction, as illustrated in (i) of FIG. 5. In such a case, a sensor 342c disposed at a right inner side of the frame 330 may sense the movement of the manipulation panel 310. The result sensed by the sensor 342c may be transmitted to the controller, and the controller may move the gantry 40 in a rightward direction as illustrated in (ii) of FIG. 5. A moving distance or a moving time of the gantry 40 may be proportional to a sensing time of the sensor 342c. For example, the gantry 40 may move in a rightward direction at a certain speed until the sensing time of the sensor 342c terminates. Additionally, or alternatively, the gantry or photograph member may be moved at a speed which reflects or is in proportion to, a degree or amount of pressure applied to the manipulation panel 310. The gantry or photograph member may be moved at a constant speed or a variable speed. Further, the gantry or photograph member may stop moving after a predetermined amount of time, after a predetermined amount of movement, and/or after the gantry has reached a limit position. In another embodiment, the direction in which the gantry or photograph member moves may be opposite to the direction in which the manipulation panel 310 is moved. For example, rightward movement of the manipulation panel 310 may result in leftward movement of the gantry or photograph member.

In the standby mode of the user control device 300, the manipulation panel 310 may be moved in a leftward direction if the user moves the manipulating means 400 in a leftward direction. In such a case, a sensor 342d disposed at a left inner side of the frame 330 may contact the manipulation panel 310 to thus sense the movement of the manipulation panel 310, and the controller may move the gantry 40 in a leftward direction in proportion to the sensing time of the sensor 342d. Additionally, or alternatively, the gantry or photograph member may be moved at a speed which reflects or is in proportion to, a degree or amount of pressure applied to the manipulation panel 310. The gantry or photograph member may be moved at a constant speed or a variable speed. Further, the gantry or photograph member may stop moving after a predetermined amount of time, after a predetermined amount of movement, and/or after the gantry or photograph member has reached a limit position. In another embodiment, the direction in which the gantry or photograph member moves may be opposite to the direction in which the manipulation panel 310 is moved. For example, leftward movement of the manipulation panel 310 may result in rightward movement of the gantry or photograph member.

Figure 6:
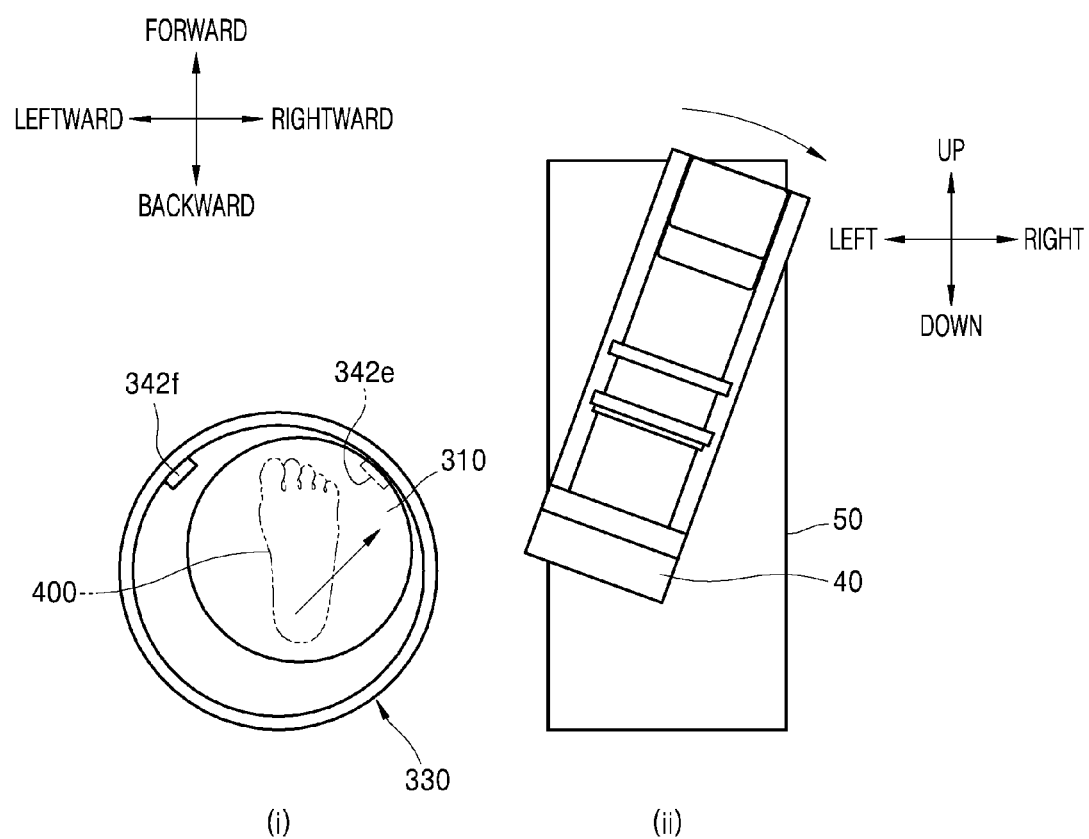
FIG. 6 is a schematic view illustrating a method of rotationally moving a gantry of the medical apparatus shown in FIG. 1 using the user control device according to an embodiment of the present invention.

FIG. 6 shows schematic views illustrating a method of rotationally moving a gantry of the medical apparatus 100 shown in FIG. 1 by using the user control device, according to another embodiment of the present invention. That is, the gantry or photograph member may be rotated in a clockwise or counterclockwise direction according to an input applied to the manipulation panel 310.

For example, when the user control device 300 is under the standby mode, the user may move the manipulating means (manipulating input) 400, such as a user's foot, in a diagonal direction between the forward direction and the rightward direction such that a sensor 342e disposed at an upper-right inner side of the frame 330 senses the movement of the manipulation panel 310, as illustrated in (i) of FIG. 6. In such a case, the controller may recognize that a user's command for rotating the gantry 40 in a clockwise direction has been inputted and may rotate the gantry 40 in a clockwise direction, as illustrated in (ii) of FIG. 6. A moving distance or a moving time of the gantry 40 may be proportional to a sensing time of the sensor 342e. For example, the gantry 40 may rotate at a certain speed in a clockwise direction until the sensing time of the sensor 342e terminates. The controller may determine a rotation angle of the gantry 40 based on the position of the sensor 342e. Additionally, or alternatively, the gantry or photograph member may be moved at a speed which reflects or is in proportion to, a degree or amount of pressure applied to the manipulation panel 310. The gantry or photograph member may be moved at a constant speed or a variable speed. Further, the gantry or photograph member may stop moving after a predetermined amount of time, after a predetermined amount of movement, and/or after the gantry or photograph member has reached a limit position. In another embodiment, the direction in which the gantry or photograph member moves may be opposite to the direction in which the manipulation panel 310 is moved. For example, an input applied in a diagonal direction between the forward direction and the rightward direction may cause the gantry or photograph member to be rotated in a counterclockwise direction.

Similarly, if the user wants to rotate the gantry 40 in a counterclockwise direction, the manipulating means 400 may be moved in a diagonal direction between the forward direction and the leftward direction in the standby mode. In such a case, a sensor 342f disposed at an upper-left inner side of the frame 330 may sense the movement of the manipulation panel 310 and the controller may rotate the gantry 40 in a counterclockwise direction. Additionally, or alternatively, the gantry or photograph member may be moved at a speed which reflects or is in proportion to, a degree or amount of pressure applied to the manipulation panel 310. The gantry or photograph member may be moved at a constant speed or a variable speed. Further, the gantry or photograph member may stop moving after a predetermined amount of time, after a predetermined amount of movement, and/or after the gantry or photograph member has reached a limit position. In another embodiment, the direction in which the gantry or photograph member moves may be opposite to the direction in which the manipulation panel 310 is moved. For example, an input applied in a diagonal direction between the forward direction and the leftward direction may cause the gantry or photograph member to be rotated in a clockwise direction.

The above-described examples are merely examples. Sensors may be disposed in other locations of the frame to sense movement of the manipulation panel and the disclosure is not limited to the example embodiments disclosed herein. The gantry (and/or other individual elements such as the x-ray generator, x-ray detector, first photograph panel, second photograph panel, and the like) may be moved in a corresponding (e.g., same) direction sensed by the sensor, or alternatively may be moved in an opposite direction.

Figure 7:
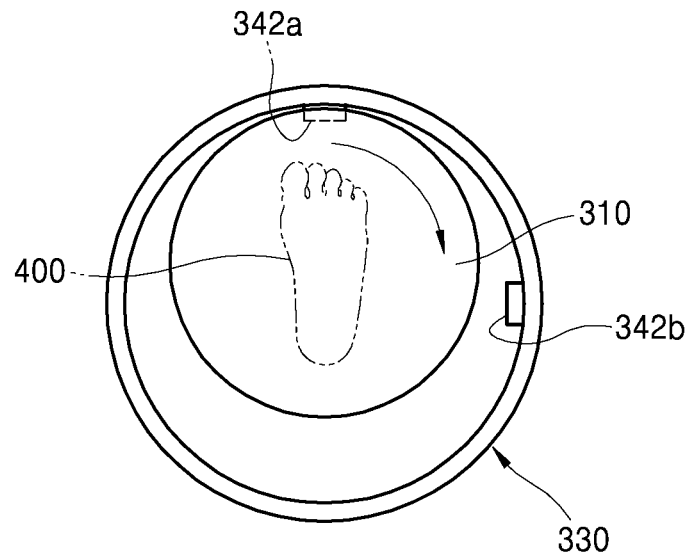
FIGS. 7 and 8 are plan views illustrating methods of rotationally moving a gantry of the medical apparatus shown in FIG. 1 using user control devices according to embodiments of the present invention.
Figure 8:
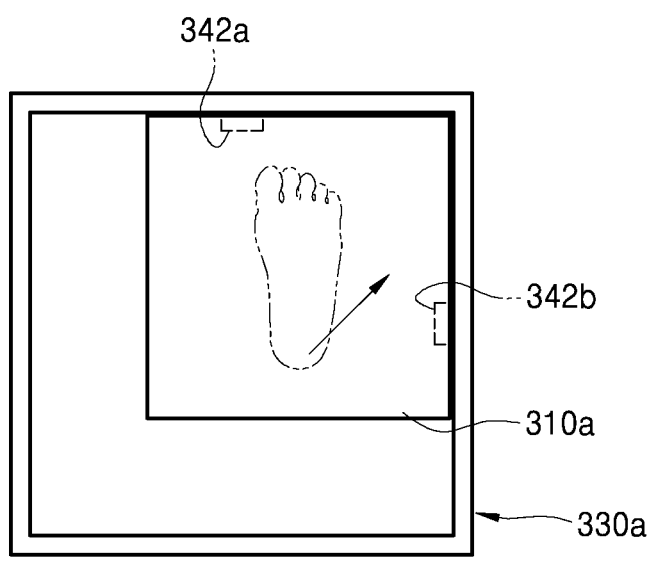

FIGS. 7 and 8 are plan views illustrating methods of rotationally moving a gantry of the medical apparatus 100 shown in FIG. 1 by using user control devices, according to some embodiments of the present invention.

The user may rotate the gantry (40 of FIG. 6) by rotating the manipulation panel 310. As illustrated in FIG. 7, a plurality of sensors 342a and 342b may be arrayed on a circle-shaped line, and the manipulation panel 310 may be rotated at a state that a portion of manipulation panel 310 contacts the sidewall 332. In such a case, sensing results of the sensors 342a and 342b may be generated to correspond to the rotating direction of the manipulation panel 310. The controller may rotate the gantry 40 according to the sensing results of the sensors 342a and 342b. That is, the gantry driver (42 of FIG. 1) may rotate the gantry 40 based on a rotating speed and a rotated angle of the manipulation panel 310.

In addition, the sensors 342a and 342b disposed at different positions may simultaneously sense the movement of the manipulation panel 310 to rotate the gantry 40. As illustrated in FIG. 8, a manipulation panel 310a and a frame 330a may have rectangular shapes when viewed from a plan view, and the sensors 342a and 342b may be disposed on sidewalls of the rectangular frame 330a. In such a case, if the manipulation panel 310a moves in a diagonal direction between a forward direction and a rightward direction, the sensors 342a and 342b disposed at a front sidewall and a right sidewall may simultaneously sense the movement of the manipulation panel 310a. As a result, the gantry driver 42 may rotate the gantry 40. A rotating angle of the gantry 40 may be proportional to a sensing time of the sensors 342a and 342b.

The gantry 40 or photograph member may be linearly or rotationally moved using the user control device 300. Alternatively, the gantry 40 or photograph member may be linearly and rotationally moved using the user control device 300. For example, if the user's foot is placed on the manipulation panel and the manipulation panel is sequentially moved in a forward direction and in a rightward direction, the gantry may be moved up and rotated in a clockwise direction. As such, since the gantry can be moved in various directions using a single user control device, the user may spatially move the gantry with ease and convenience.

Again, the above-described examples are merely examples. Sensors may be disposed in other locations of the frame to sense movement of the manipulation panel and the disclosure is not limited to the example embodiments disclosed herein. The gantry (and/or other elements such as the x-ray generator, x-ray detector, first photograph panel, second photograph panel, and the like) may be moved in a corresponding (e.g., same) direction sensed by the sensor, or alternatively may be moved in an opposite direction. Further, the frame and manipulation panel may have the same shape but need not have the same shape. Further, the frame and manipulation panel may be shaped in other geometric forms and is not limited to those specifically disclosed herein. By way of example, the frame and manipulation panel may be circular, oval-shaped, triangular, rectangular, or any polygonal or geometric shape.

Figure 9:
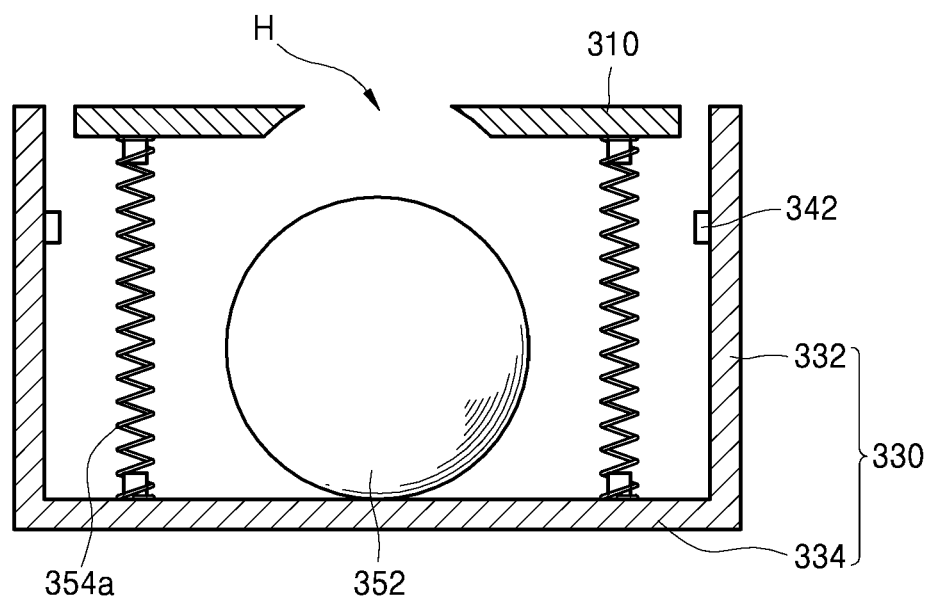
FIGS. 9 and 10 are cross-sectional views illustrating a user control device according to embodiments of the present invention.
Figure 10:
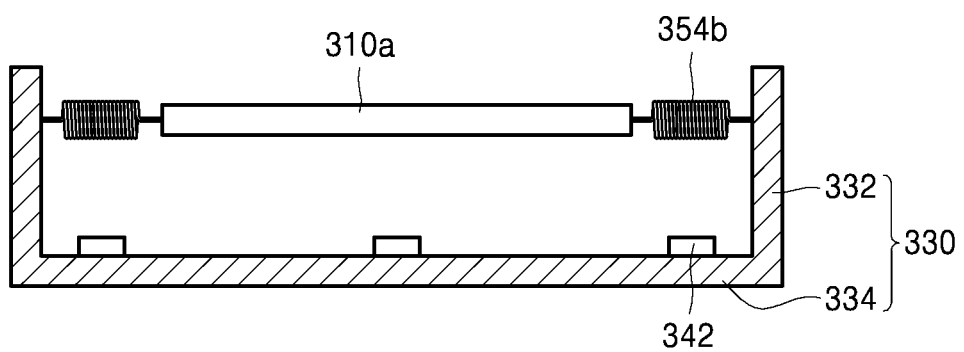

FIGS. 9 and 10 are cross-sectional views illustrating a user control device according to an embodiment of the present invention.

As illustrated in FIG. 9, an auxiliary unit 350 of a user control device 300 may be configured to include only a supporting unit 352 and elastic units 354a. If no pressure is applied to the manipulation panel 310, the supporting unit 352 may be spaced apart from the manipulation panel 310 by a predetermined distance due to an elastic force of the elastic units 354a. A unit of the supporting unit 352 may protrude upwardly from the manipulation panel 310 through a hole H of the manipulation panel 310. In such a case, a movement of the supporting unit 352 may be limited even when a user control device 300 is under an initial mode. If the manipulating means (manipulation unit) 400 (see FIG. 4) is placed on the manipulation panel 310, the hole H of the manipulation panel 310 may be filled with the supporting unit 352. While the manipulating means (manipulation unit) 400 is placed on the manipulation panel 310, the user may move the manipulation panel 310 in at least one direction among various directions including a forward direction, a backward direction, a leftward direction, a rightward direction, and a rotating direction.

As illustrated in FIG. 10, an auxiliary unit 350 of a user control device 300 may be configured to include only an elastic unit 354b. The elastic unit 354b may connect a side portion of the manipulation panel 310a to a sidewall 332 of the frame 330, and sensors 342 may be disposed on the bottom portion 334 of the frame 330. The user may put a manipulating means (manipulation unit) 400 on the manipulation panel 310a such that the manipulation panel 310a contacts the bottom portion 334 of the frame 330. Thereafter, the user may move the manipulation panel 310a in at least one direction among various directions including a forward direction, a backward direction, a leftward direction, a rightward direction and a rotating direction, thereby inputting user's commands into the controller of the medical apparatus.

The user control device and the medical apparatus according to the present disclosure may move a control target of the medical apparatus in response to the user's movement. Thus, the user may more readily handle or operate the medical apparatus.

Although the present disclosure is described in conjunction with the mammography apparatus, the inventive concept is not limited to thereto. The inventive concept may be equally applicable to other medical apparatuses, for example, magnetic resonance imaging (MRI) apparatuses, computed tomography (CT) apparatuses, or the like.

It is noted that the medical or radiological imaging apparatus (e.g., mammography apparatuses, X-ray apparatuses, MRI apparatuses, CT apparatuses, and the like) according to the example embodiments disclosed herein may be applied to a target object including a human, an animal, or other life form, or to any other objects for which imaging may be applied (e.g., security applications such as airport security or border security, industrial applications such as taking x-ray images of welds, art applications such as taking x-ray images of paintings, etc.).

The medical or radiological imaging apparatus and methods of implementing the medical or radiological imaging apparatus according to the above-described example embodiments may use one or more processors, which may include a microprocessor, central processing unit (CPU), digital signal processor (DSP), or application-specific integrated circuit (ASIC), as well as portions or combinations of these and other processing devices.

Methods for controlling a medical or radiological imaging apparatus according to the above-described embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules that are recorded, stored, or fixed in one or more computer-readable storage media, in order to perform the operations of the above-described embodiments, or vice versa. The program instructions may be executed by one or more processors. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA).

While example embodiments have been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A user control device for a medical apparatus, the device comprising:
   a manipulation panel including a hole in a central portion thereof;
   a frame spaced apart from the manipulation panel and including a bottom portion and a sidewall upwardly protruding from an edge of the bottom portion;
   an auxiliary unit disposed in an interior portion of the frame and including a supporting unit disposed at a position corresponding to the hole, to assist movement of the manipulation panel; and
   a sensing unit to sense a movement of the manipulation panel,
   wherein
   the manipulation panel is three-dimensionally movable according to a movement of an external manipulator applied to the manipulation panel.

2. The device of claim 1,
   wherein
   the supporting unit contacts the bottom portion of the frame if the external manipulator applies a force to the manipulation panel, and
   the supporting unit is spaced apart from the bottom portion of the frame if the force applied by the external manipulator is removed from the manipulation panel.

3. The device of claim 2, wherein the manipulation panel is movable in a horizontal direction parallel with the bottom portion of the frame or in a vertical direction parallel with the sidewall of the frame.

4. The device of claim 1, wherein the manipulation panel has a flat board shape.

5. The device of claim 1, wherein the sensing unit is disposed on at least one of the frame and the manipulation panel.

6. The device of claim 1,
   wherein the supporting unit comprises a spherical ball.

7. The device of claim 1,
   wherein
   the manipulation panel contacts the supporting unit if the external manipulator applies a force to the manipulation panel, and
   the manipulation panel is spaced apart from the supporting unit if the force applied by the external manipulator is removed from the manipulation panel.

8. The device of claim 1, wherein the auxiliary unit includes an elastic unit that returns the manipulation panel to an original position when a force applied by the external manipulator is removed from the manipulation panel.

9. The device of claim 1, wherein the device spatially moves at least one element of the medical apparatus in response to movement of the manipulation panel.

10. The device of claim 1, wherein the external manipulator includes a foot of a user.

11. A medical apparatus comprising:
    a user control device including a manipulation panel including a hole in a central portion thereof and a frame spaced apart from the manipulation panel and including a bottom portion and a sidewall upwardly protruding from an edge of the bottom portion;
    an auxiliary unit disposed in an interior portion of the frame and including a supporting unit disposed at a position corresponding to the hole, to assist movement of the manipulation panel; and
    a driver to spatially move photograph members in response to movement of the manipulation panel.

12. The medical apparatus of claim 11, wherein the manipulation panel is three-dimensionally moveable.

13. The medical apparatus of claim 11, wherein the photograph members linearly move if the manipulation panel linearly moves.

14. The medical apparatus of claim 11, wherein the photograph members rotate if the manipulation panel rotates.

15. The medical apparatus of claim 11:
    wherein if the manipulation panel moves in a first direction, the photograph members move in a second direction; and
    wherein if the manipulation panel moves in a third direction different from the first direction, the photograph members move in a fourth direction different from the second direction.

16. The medical apparatus of claim 15, wherein if the manipulation panel moves in a direction between the first direction and the third direction, the photograph members rotate.

17. The medical apparatus of claim 15, wherein the manipulation panel moves in the first or the second direction after moving the manipulation panel toward the bottom portion of the frame.

18. The medical apparatus of claim 11,
    wherein
    the supporting unit contacts the bottom portion of the frame if an external manipulator applies a force to the manipulation panel, and
    the supporting unit is spaced apart from the bottom portion of the frame if the force applied by the external manipulator is removed from the manipulation panel.

19. The medical apparatus of claim 11, wherein the auxiliary unit further includes an elastic unit that returns the manipulation panel to an original position if a force applied by the external manipulator to the manipulation panel is removed from the manipulation panel.

20. A user control device comprising:
a frame including a bottom portion and at least one side wall extending upward from the bottom portion;
a manipulation panel, including a hole in a central portion thereof, to move three-dimensionally according to an external force applied to the manipulation panel;
an auxiliary unit connected to the frame and disposed within an inner portion of the frame and including a supporting unit disposed at a position corresponding to the hole, to support movement of the manipulation panel; and
at least one sensor disposed within the frame to sense movement of the manipulation panel,
wherein the user control device is configured to control movement of one or more elements of a medical apparatus based on movement of the manipulation panel sensed by the at least one sensor.

21. The user control device of claim 20, wherein the auxiliary unit further includes an elastic unit to return the manipulation panel to an original position after the external force applied to the manipulation panel is removed.

22. The user control device of claim 21, wherein
the supporting unit and manipulation panel are spaced apart from one another when the external force applied to the manipulation panel is removed, and
the manipulation panel moves toward the supporting unit to contact the supporting unit when the external force is applied to the manipulation panel.

23. The user control device of claim 22, wherein the auxiliary unit further includes a connecting unit to surround at least a portion of the supporting unit, wherein the elastic unit is fixed to the connecting unit.

24. A method of controlling movement of at least one photograph member disposed at a medical apparatus, the method comprising:
receiving a force by a manipulation panel of a user control device connected to the medical apparatus, thereby causing the manipulation panel to contact a supporting unit of the user control device and causing the supporting unit to contact a bottom portion of a frame of the user control device;
sensing, by at least one sensor disposed within the frame of the user control device, a movement direction of the manipulation panel;
in response to the at least one sensor sensing the supporting unit contact the bottom portion of the frame, changing a mode of the user control device from an initial mode to a first mode; and
after the user control device is changed into the first mode, controlling the at least one photograph member to move in a predefined direction in response to the at least one sensor sensing a subsequent movement of the manipulation panel.

25. The method of claim 24, further comprising:
transmitting, by the user control device, a command to a driver of the medical apparatus to move the at least one photograph member; and
moving, by the driver, the at least one photograph member for a time or distance proportional to a sensing time of the at least one sensor.

* * * * *